United States Patent [19]

Hajicek

[11] Patent Number: 4,935,884
[45] Date of Patent: Jun. 19, 1990

[54] SONIC PIPE LENGTH DETECTOR

[75] Inventor: David J. Hajicek, Minnetonka, Minn.

[73] Assignee: Champlin Electronics, Inc., Champlin, Minn.

[21] Appl. No.: 187,328

[22] Filed: Apr. 28, 1988

[51] Int. Cl.⁵ .................. G01B 17/00; G01N 29/00
[52] U.S. Cl. ............................ 364/562; 73/631; 364/506; 364/571.03; 367/98; 367/127; 367/900; 367/902; 367/911
[58] Field of Search ............... 367/13, 82, 98, 99, 367/108, 115, 116, 127, 140, 900, 902, 910, 911; 364/505, 506, 550, 562, 571.03; 73/12, 1 DV, 626, 638, 629, 631

[56] References Cited

U.S. PATENT DOCUMENTS

| | | | |
|---|---|---|---|
| 3,982,425 | 9/1976 | McLain | 364/506 |
| 4,229,796 | 10/1980 | Garrett | 364/506 |
| 4,234,942 | 11/1980 | Prause et al. | 364/562 |
| 4,241,430 | 12/1980 | Kayem et al. | 367/99 |
| 4,264,788 | 4/1981 | Keldel et al. | 367/99 |
| 4,334,431 | 6/1982 | Kohno et al. | 73/597 |
| 4,393,711 | 7/1983 | Lapides | 73/1 DV |
| 4,420,824 | 12/1983 | Weber | 367/108 |
| 4,451,909 | 5/1984 | Kodera et al. | 367/99 |
| 4,464,738 | 8/1984 | Czajkowski | 367/108 |
| 4,466,286 | 8/1984 | Berbee et al. | 73/629 |
| 4,494,224 | 1/1985 | Morrell et al. | 367/99 |
| 4,510,810 | 4/1985 | Kanda et al. | 73/626 |
| 4,523,468 | 6/1985 | Derkacs et al. | 73/628 |
| 4,584,676 | 4/1986 | Newman | 367/108 |
| 4,619,143 | 10/1986 | Franken | 73/629 |
| 4,630,226 | 12/1986 | Tanaka | 367/127 |
| 4,675,854 | 6/1987 | Lau | 367/98 |
| 4,677,599 | 6/1987 | Obayashi et al. | 367/98 |
| 4,719,605 | 1/1988 | Eder et al. | 367/99 |
| 4,733,668 | 3/1988 | Torrence | 73/631 |
| 4,735,088 | 4/1988 | Pinyan et al. | 367/902 |
| 4,799,387 | 1/1989 | Matsuo | 73/629 |

Primary Examiner—Kevin J. Teska
Attorney, Agent, or Firm—Schroeder & Siegfried

[57] ABSTRACT

An apparatus for determining the length of an open or closed-end pipe by measuring the propagation delay of a sound pulse transmitted down the pipe bore. The apparatus includes an acoustic transducer, an acoustic detector and associated circuitry for computing the time required for an acoustic pulse to travel and return the length of a pipe. Electronic circuitry, including a microprocessor, is employed to provide the apparatus with an automatic gain adjustment feature. The gain circuitry increases the amplification until a return pulse of desired amplitude is obtained. The gain is time varying to make the last-to-return signals strongest thereby avoiding false readings from pipe discontinuities. Compensation is made for speed-of-sound variations due to temperature, humidity, and barometric pressure by direct measurement of speed of sound during each length measurement. The open or closed endedness of a pipe is determined by return signal charateristics and a correction factor applied for open-ended pipe.

15 Claims, 5 Drawing Sheets

0
SONIC PIPE LENGTH DETECTOR

BACKGROUND OF THE INVENTION

This invention relates generally to apparatus and methods for determination of pipe length. Specifically, the invention relates to an apparatus and method for determining the length of pieces of pipe by employing sonic waves.

Accurately determining the length of pieces of pipe is very important in many industries. In the oil industry, for example, standard thirty-foot lengths of pipe are threaded and used in the drilling of oil wells. Upon reuse the worn threads or couplings may be cut off, thereby shortening the length of pipe. The price of pipe and installation thereof is based on a dollar amount per linear foot. Therefore, an accurate determination of the length of pipe is needed for payment to the oil drilling operator. In many other industries such as irrigation, well drilling, and steam fitting the length of pipe used is also very important.

In the oil industry, it is common practice to remove from the ground and store on end approximately 90 foot sections of pipe on an oil drilling platform A 90 foot section is composed of three 30 foot sections coupled together. What is needed is a method to determine exactly the length of removed pipe. One method that has been tried is the use of a laser. This necessitates the placement of a mirror at one end of a pipe and a apparatus containing a laser at the other end and a means for determining the time of flight for light to pass from one end of the pipe to the receiving unit at the same end of the pipe as the laser unit These units have not been successful because of their difficult use and high cost. It requires a placement of a mirror at one end of the pipe which is not possible with pipe standing vertically, and even when sections are laid horizontally, it does not permit ease of operation by one person.

Various schemes have been tried to sonically measure the length of pipe such as the method disclosed in U.S. Pat. No 4,241,430 to Kayem et al. The Kayem et al Patent discloses the use of a source/detector which mechanically couples to the pipe to be measured and sends out an acoustic signal. The teachings of Kayem et al are herein incorporated by reference. The sound echo returning from the far end of the pipe is sensed and based on its time of travel gives a measurement of the pipe length. Compensation for the speed of sound is made by measuring the air temperature. This causes large inaccuracies due to the difference between measured temperature of the air versus the actual temperature of the air in the pipe. In addition, relative humidity and barometric pressure factors are not accounted for in the Kayem et al invention. The apparatus as disclosed does not take into account any difference in the pipe being open-ended or closed-ended. As mentioned earlier, in an oil drilling operation, oil pipe is often stored on a drilling platform having a wooden or metal floor The pipe is stored vertically on end on the platform and this effectively makes for a closed end condition.

U.S. Pat. No. 4,584,676 to Newman is directed to a method and apparatus for pipelength measurement which tries to correct for some of the inaccuracies which were not addressed in the Kayem et al Patent. Newman recognizes the use of mechanical compensation for open-ended pipe measurement. The teachings of Newman are herein incorporated by reference. The open air coupling method he uses is prone to receive ambient noise such as passing trucks, drilling rig operation and other sound waves which may give rise to false readings. No accurate method of determining the speed of sound is made other than temperature measurements. The amplification and detection system is not able to handle problems of pipe couplings near the source or connectors within a string of pipe, all of which may give rise to false echoes.

What is needed for practical application is a pipe-length detection system capable of measuring pipe-length length to the nearest ¼ inch in 90 feet under dirty conditions with multiple pipe sections, including couplings at the source end of the pipe. The system must be able to measure both open-ended and closed-ended pipes and be able to do so under real world operating conditions.

SUMMARY OF THE INVENTION

The present invention comprises a sonic transducer having a built-in reference calibration which can be inserted into one end of a pipe to be measured to accurately determine its length. Upon activation a sonic wave emanates from the main transducer into the pipe to be measured. The sonic wave hits discontinuities in the pipe including the end of the pipe. Electronic circuitry associated with a receiver located in the transducer detects the signal reflected from discontinuities in the pipe. If the waveform of the signal has the proper amplitude and periodicity, as determined by a microprocessor, the length of the pipe is calculated. The transducer is made to physically abut an end of pipe to be measured and the open end of the transducer "decoupler" is angled in a beveled shape to provide a non-resonant acoustic coupling between the transducer and the air in the pipe. At the same time, the decoupler isolates or decouples the transducer from unwanted reflections at the near end of the pipe including the pipe coupling, if any. Located within the decoupler with a known spacing from the sound source are one or two microphones. For each measurement of pipe length the speed of sound is accurately determined within the pipe and stored in the microprocessor by noting the time taken for sound to travel a known distance.

An analog time varying gain amplifier is used to amplify the signal received from the far end of the pipe with gain increasing with time, since the longer the pipe the smaller the returning signal from the far end. Digital circuitry selects additional fixed gain amplification as needed to meet the required threshold voltage criteria for a valid return signal and determines the timing of zero crossings of the return signal from which the timing can be measured to determine the length of pipe. The polarity of the return signal waveform indicates an open or closed-ended pipe. A negative going waveform, that is opposite in sign from the source pulse, indicates an open-ended pipe for which a correction is needed.

DETAILED DESCRIPTION OF THE PREFERRED EMBODIMENT

Figure 1A:
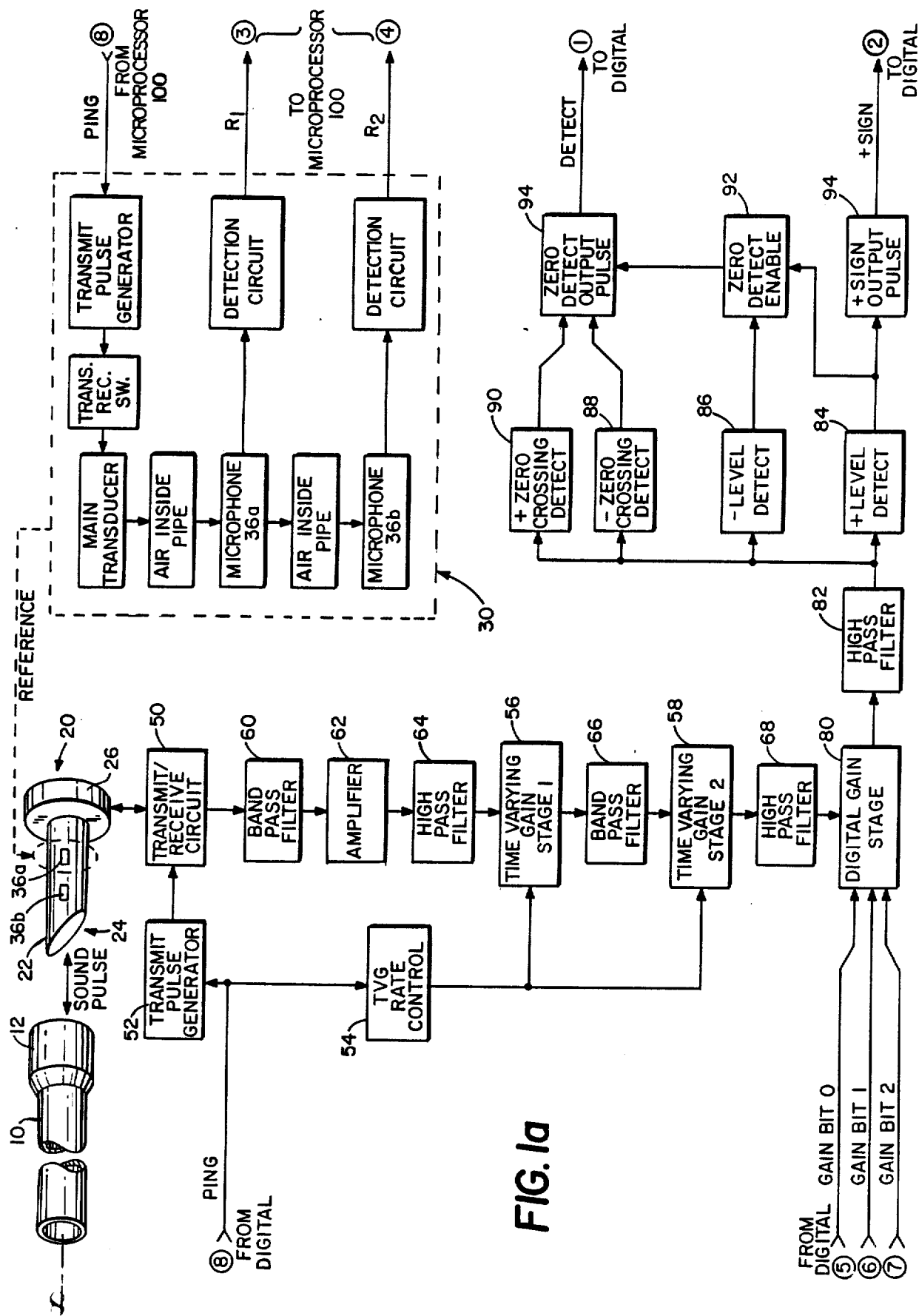
FIG. 1a and 1b, are block diagram views of the apparatus and steps used in determining the length of pipe by sonic means.
Figure 1B:
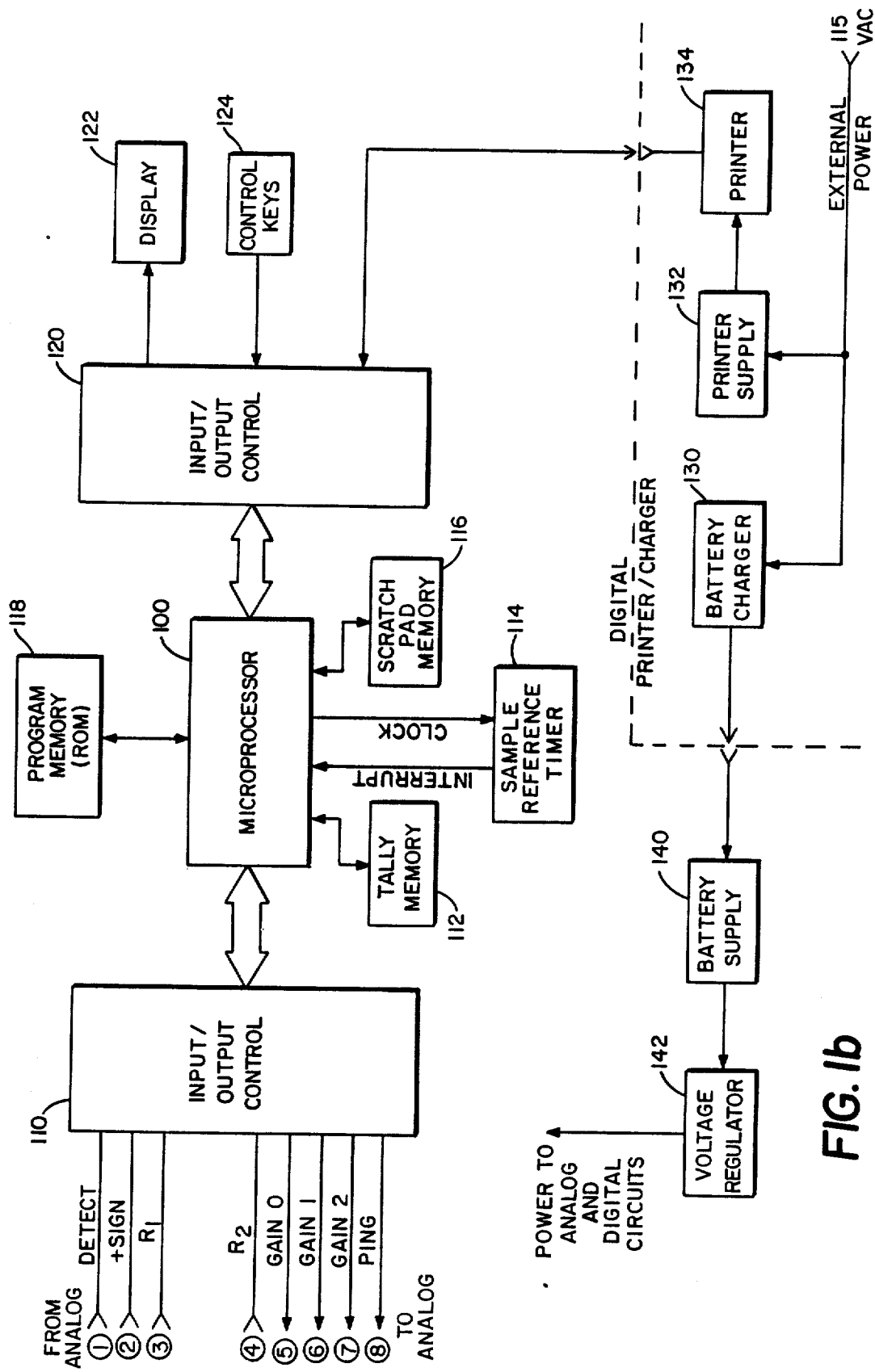

Referring to FIG. 1a and 1b there is shown in block diagram form the apparatus for sonic pipe length detection. The pipe to be measured 10 is shown with collar 12 for coupling to additional pipes. The main transducer 20 is adapted to mate with pipe 10 by abutting collar 12, but will work equally well with pipe with no collar or with other end treatment. The main transducer has a snout 22 with a beveled end 24. Housing 26 contains the electronics or connections for electronics to the snout. An optional cone-shaped element 28, shown in FIG. 4, which can be a silicone washer, provides the stop against which the main transducer will butt against the pipe to be measured. Contained within the snout of the main transducer is a speed of sound reference system.

Figure 5A:
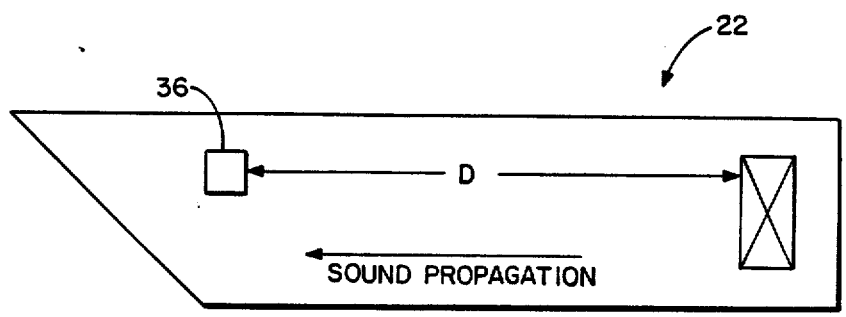
FIG. 5a and 5b are detailed drawings of the speed of sound reference.
Figure 5B:
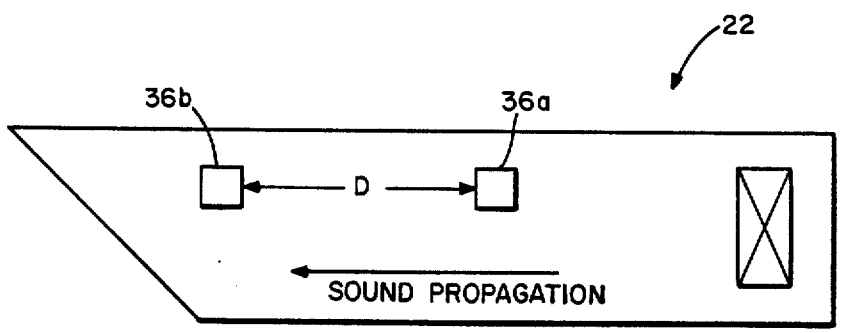

The speed of sound reference shown in 5a and 5b contains one or two microphone/receivers 36 spaced-apart from the main transducer element with known spacing D. Operation for the sound reference in FIG. 5b will be described, as 5a is similar. The speed-of-sound reference system 30, as shown in FIG. 1, consists of the following. The main transducer generates a sonic pulse which propagates down the snout at the speed of sound as determined by the air in the pipe. When the pulse reaches microphone 36a, the detection circuit generates a time reference pulse R1 to the mircroprocessor 100, which starts elapsed time measurement. When the pulse reaches microphone 36b the detection circuit generates a second time pulse R2 to the microprocessor which halts elapsed time measurement. The elapsed time between when the sonic pulse reaches microphones 36a and 36b divided by the distance D between the microphones is the speed of sound. Electronic signal timing reference criteria may be either amplitude level or zero crossing. With one microphone, as shown in FIG. 5a, the main transducer pulse would begin propagation measurement timing. The two microphone system of FIG. 5b is less sensitive to variations in main transducer operational characteristics. The microprocessor 100 calculates the speed of sound for the air in the pipe by elapsed time to propagate a known distance. This information is stored in the microprocessor to be used in calculating the pipe length after measuring the time for the sonic wave to travel from the main transducer output to the end of the pipe and back.

The sequence of events within the sonic pipelength detector is controlled by microprocessor 100 which sends a signal from its digital output as a ping on line 8 to the analog transmit pulse generator 52 which in turn sends the transmit pulse through from the transmit/receive circuit 50. The transmit/receive circuit is set first to transmit and then to receive. At the same time the time varying gain rate control 54 is initiated at the minimum gain setting. The time varying gain control 54 is used to control both a first stage time varying gain 56 and a second stage time varying gain control 58 which are multiplied together to produce a very high total gain amplification of the return signal.

The return signal is received from the main transducer through the transmit/receive circuit 50 and passed through a band pass filter 60. After an initial filtering the signal is amplified by amplifier 62 and filtered additionally by high pass filter 64. The signal is then amplified by the first stage of the time varying gain 56 and filtered again by band pass filter 66 from which the signal enters the second stage time varying gain amplifier 58. From the second stage of the time varying gain the signal is filtered once again in high pass filter 68 before entering the digital gain stage 80.

Figure 3A:
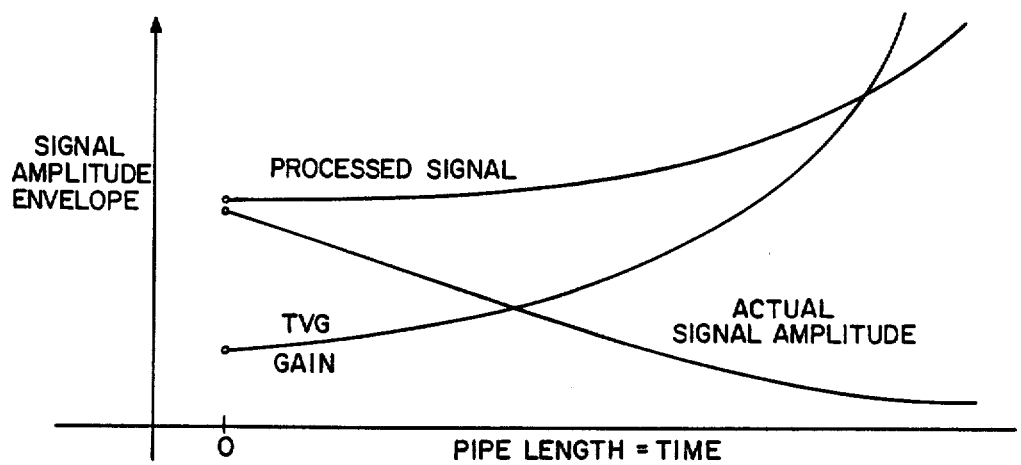
FIG. 3a and 3b are drawings showing the echo signal, the time varying gain, and the processed signal.

Shown in FIG. 3a is the raw signal level without correction versus time (T) which is proportional to distance. The raw signal starts out at time equal to 0 and decays in an exponential fashion. The time varying gain amplification employed in the invention more than counteracts this exponential decay and makes the signal returning from the further distance stronger than the signal returning from closer distances to the source of the sonic signal. The processed signal shown is a product of the raw signal received from reflections along the pipe and the time varying gain amplification.

Figure 2A:
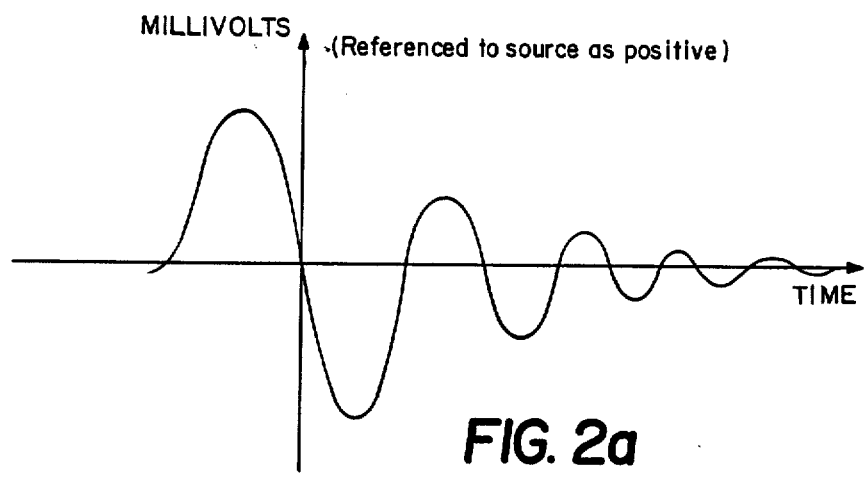
FIG. 2a and 2b are drawings of the return waveform from a closed-end pipe and an open-ended pipe respectively.
Figure 2B:
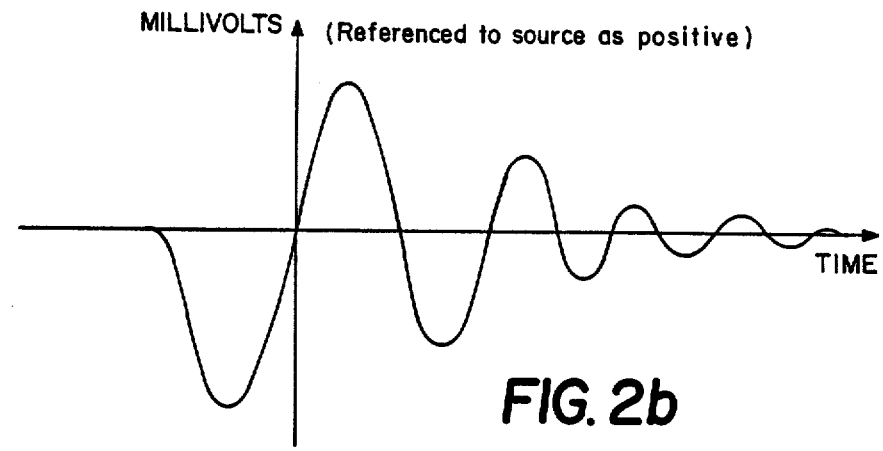

The return signal from discontinuities in the pipe looks like that shown in FIG. 2a which is for a length of pipe having a closed end. The signal looks like a decaying oscillation. To ensure that a signal is valid, some threshold value or limit has to be met. For this invention the preferable threshold value has been chosen to be 200 millivolts for a valid return signal. The time between the oscillations is detected by a zero-crossing detector. The shape of the oscillations for a valid signal will be first positive-going (positive meaning the same polarity as the source) and then negative going crossing through zero and rising again for a closed-end pipe as shown in 2a. For an open-ended pipe the return signal will be first negative-going then positive going crossing through zero and then decaying negatively through zero again as shown in FIG. 2b. It is a system requirement that threshold values be met in both the positive and negative going directions for a valid return signal.

Figure 3B:
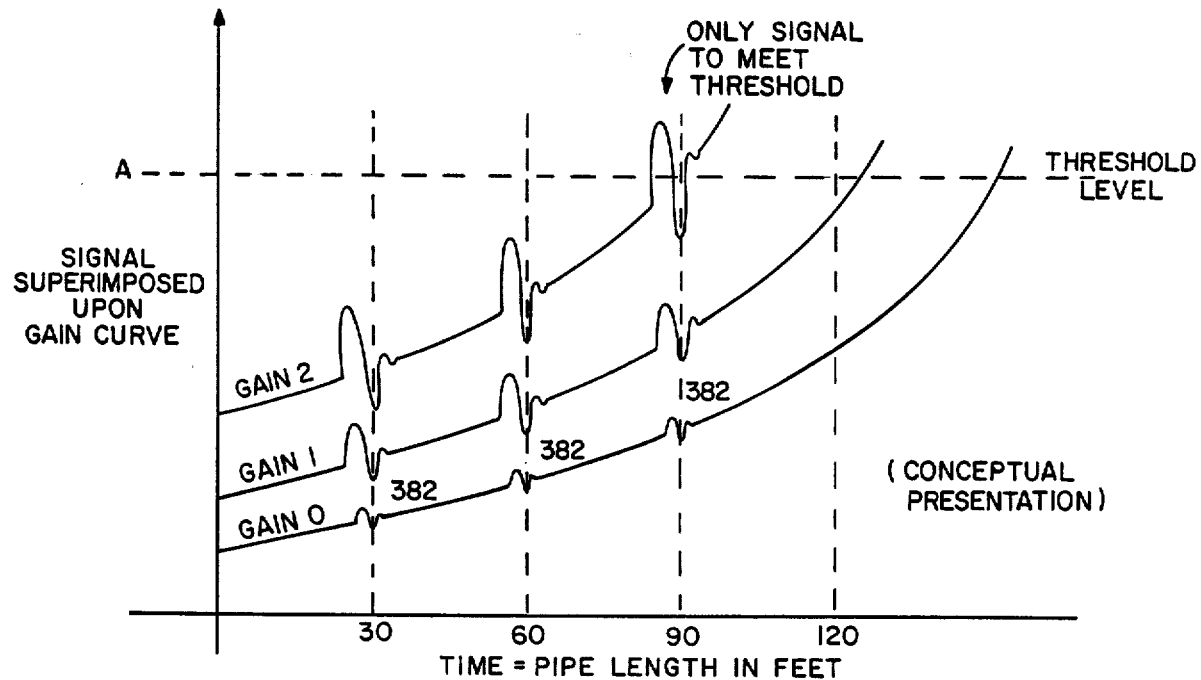

Lengths of oil pipe are generally 30 feet. The lengths are threaded together to make one continuous casing of pipe for oil drilling. When the oil pipe is pulled from the well, such as to change drilling bits, the pipe is often pulled and decoupled in approximately 90 foot sections to save the time and effort required in dealing with just 30 foot sections. Therefore, if 90 foot sections of pipe are desired to be measured the sections will contain coupling and threads between approximately 30 foot lengths. Any discontinuities such as threads, couplings, or dirt in a pipe will send off reflective sonic signals which will be received by the transducer/receiver unit. To prevent the system from picking the reflected signals from pipe discontinuities as the determining signals for the length of the pipe, a digital gain stage is an employed. The digital gain stage 80 works in conjunction with the analog time varying gain to provide accurate determination of the real end of pipe return echo. This is shown in FIG. 3b where the digital gain stage is set at a first value which will be too low for most typical pipe lengths. Assuming a 90 foot pipe section, the first digital gain setting as shown in FIG. 3b is 0. Three echoes labeled 382 are shown in FIG. 3b. The echo responses are from the first 30 foot section of pipe, the second 30 foot section of pipe and the end of the pipe, respectively. None of the signals rise above the threshold of 200 millivolts which is labeled A. Since no valid return signals were received, a new ping is sent out with a digital gain setting of 1. The return echoes as shown in FIG. 3b along curve gain 1 fail to meet the threshold value. Since no valid return signal was received, a third gain setting (curve gain 2) is employed and produces a return signal above the threshold voltage for the return signal reflected from the end of the 90 foot pipe. The digital gain setting has been chosen to have 8 different settings and to employ an exponentially increasing gain. For example, if a gain ratio of 2:1 was chosen between gain 0 and gain 1, this would provide a 256 times increase in gain from the lowest value to its highest value.

From the digital gain stage 80 the signal goes through high pass filter 82 and on to the signal level and zero crossing detectors. The signal must be higher than the preset threshold value, in this case 200 millivolts, in both the positive going waveform level detector 84 and the negative waveform level detector 86. The positive going zero-crossing is detected by detector 90 and the negative going zero-crossing detected by detector 88. Once the threshold value is satisfied in detectors 84 or 86 the zero crossing detection signals are enabled by gate 92 which enables the zero detector output pulse 94. The detect signal is sent to line 1 of the input/output controller 110 (shown in FIG. 1b). If the waveform of the signal is positive it will be detected by the sign output pulse detector 94 and a pulse will be sent by the + signal line 2 to the input/output control 110.

As shown in FIG. 1b, microprocessor 100 has a tally memory 112, a sample reference timer 114 which acts as a clock, a scratch pad memory 116, a program memory ROM 118, and a second input/output controller 120 which can be used to operate a display 122 and has input control keys 124. External power is provided from line voltage and can be used to operate a battery charger 130 or power a printer supply 132 which drives printer 134. The battery charger can be used to charge battery supply 140 whose output goes to a voltage regulator 142 to power the analog and digital circuits.

Figure 4:
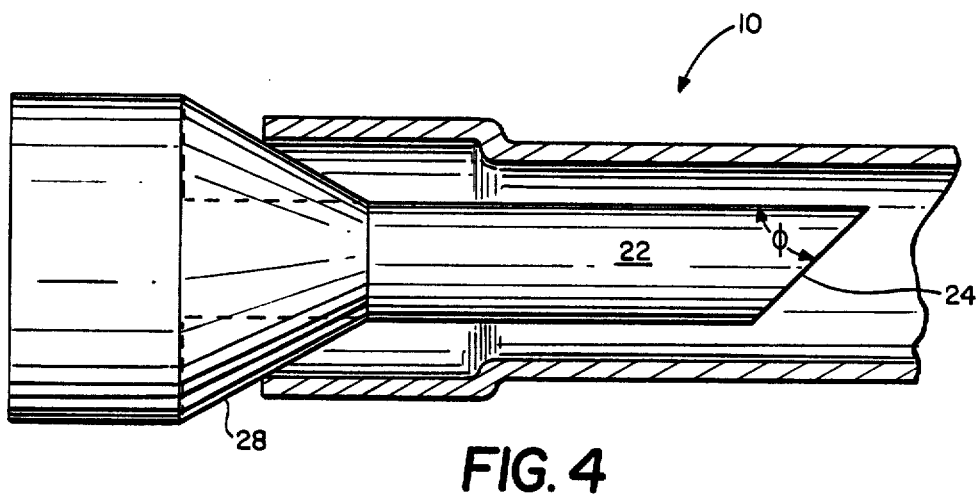
FIG. 4 is a close-up of the source/detector showing in detail the transducer snout.

In pipes having a closed end a reflection from the come from the closed off end, and provide accurate length measurements. It is known, as discussed U.S. Pat. No. 4,241,430 to Kayem et al, that the measurements of pipe having open ends will be off by an amount generally related to the diameter of the pipe. That is, reflections from an open ended pipe will appear to come from a distance past the end of the pipe. To correct for this problem the invention employs an optional conical shaped element between the main transducer element and the end of the pipe to which the transducer element is abutted. Shown in FIG. 4 is an enlarged detail of the snout 22 of the main transducer element 20. The pipe 10 to be measured has inserted into it snout 22. Conical resilient member 28 is mounted with a cone angle and stand-off calculated to adjust for different diameters of pipe and couplings so that once it is determined that the pipe is open-ended the same correction factor can be applied to the length calculations to produce an accurate pipe length measurement independent of pipe diameter. The alternate approach is to tell the microprocessor the pipe diameter and allow the microprocessor to apply an open-ended pipe correction factor to the length automatically.

An important feature of the snout tip 22 is the beveled edge 24 which provides for a gradual coupling of the sonic wave into the pipe so that little or no reflections are received from the snout opening itself. This configuration also decouples the received signal from reflections generated by the pipe coupling at the source. It is desirable that the bevel be long enough to be on the order of a wavelength of the sound frequency of the sonic wave being used in the invention. An included angle 0 preferably of thirty degrees or less would be an appropriate choice, although greater angles work with decreased effectiveness.

The circuitry and physical components of the present invention may be arranged and constructed in different forms to accomplish the improved method and apparatus of pipe measurement according to this invention. Therefore, it is believed that the foregoing disclosure and description of the invention are illustrative and explanatory of the various components and circuitry that may be used within the scope of the appending claims without deporting from the spirit of the invention.

What is claimed is:

1. A method of determining the length of a pipe comprising the steps of;
    (a) sending an acoustic signal down the length of pipe via a sonic transducer;
    (b) determining the speed of sound based on a measured time it takes for said acoustical signal to travel a known distance;
    (c) detecting a reflected acoustic signal from the end of the pipe, said reflected signal being required to acquire a predetermined threshold voltage level for detection thereof;
    (d) detecting zero crossings of said reflected acoustic signal;
    (e) determining a time lapsed between sending said acoustic signal and detecting said zero crossing of said reflected acoustic signal;
    (f) calculating a corrosion factor for the length of pipe if open ended, the determination of open-endedness based on the shape of said reflected acoustic signal; and
    (g) determining the length of the pipe as a function of said determined speed of sound and said time lapse between sending said acoustic signal and detecting said zero crossing of said reflected acoustic signal, taking into account said correction factor if necessary.

2. The method of claim 1 wherein said reflected acoustic signal is processed by a time varying gain amplifier prior to detection of said reflected acoustic signal.

3. The method of determining the length of a pipe in claim 1, and detecting the polarity of said reflected acoustic signal at said zero crossings to determine the shape of said reflected acoustic signal and consequently whether the pipe is open-ended or close-ended.

4. The structure defined in claim 1, wherein said polarity detector detects whether said reflected acoustical signal is negative-going or positive-going at said zero crossings.

5. An apparatus for use in collecting data for measuring the length of an open or close-ended pipe having a near and far end, comprising:
    (a) a sonic transducer assembly adapted to be inserted into the near end of the pipe to be measured and constructed and arranged to transmit an acoustical signal down the length of the pipe for reflection thereof from the far end of the pipe;
    (b) a time varying amplifier means for receiving and amplifying said acoustical signal after reflection thereof from the far end of the pipe, thereby defining an amplified reflected acoustical signal;
    (c) a threshold limit comparator means electrically connected to said amplifier means and constructed and arranged to determine whether said reflected acoustical signal received by said amplifier means is of a sufficient signal level to qualify as a valid reflected acoustical signal from the end of the pipe; and (d) a detector means including a zero crossing and polarity detector electrically connected to said amplifier means for determining the travel time of said acoustical signal from said sonic transducer to the far end of the pipe and back to said sonic tranducer, and for determining the polarity of said reflected acoustical signal, the polarity of said reflected acoustical signal being indicative of the far end of the pipe being closed or open.

6. The apparatus of claim 5, including a microprocessor which is electrically connected to said detector means and said threshold limit comparative means, said microprocessor being constructed and arranged to receive information therefrom regarding said reflected acoustical signal so as to calculate the length of the pipe, subtracting a correction factor from the determined length of pipe when the far end of the pipe is detected as being open.

7. The apparatus of claim 5 wherein said sonic transducer has an angled snout to minimize undesirable reflections of sound near said sonic transducer.

8. The apparatus of claim 5 wherein said reflected acoustical signal is an acoustical wave having both positive and negative peak amplitudes, and said threshold limit comparator means is constructed and arranged to require both said positive and negative peak amplitudes of said reflected acoustical signal to meet a predetermined threshold signal level to be a valid reflected acoustical signal.

9. The apparatus of claim 5, including a speed of sound reference detector which is activated for each measurement, said speed of sound reference detector comprising said sonic transducer and two microphones, said microphones being spaced at a predetermined fixed distance from each other, and being disposed in confronting relation to said acoustical signals transmitted from said sonic transducer.

10. The structure defined in claim 5, wherein detection of said zero crossing of said reflected acoustical signal by said zero crossing detector determines the end of the travel time of said acoustical wave.

11. The apparatus of claim 5, including a speed of sound reference detector which is activated for each measurement, said speed of sound reference detector comprising said sonic transducer and one microphone, said microphone being spaced from said sonic transducer at a predetermined fixed distance and disposed in confronting relation to said acoustical signal transmitted from said sonic transducer.

12. The apparatus of claim 11, including a microprocessor which is electrically connected to said speed of sound reference detector, said zero crossing and polarity detector means, and said threshold limit comparator means, said microprocessor being constructed and arranged to receive information therefrom regarding said reflected acoustical signal so as to calculate the length of the pipe, subtracting a correction factor from the determined length of pipe when the far end of the pipe is detected as being open.

13. The apparatus of claim 5 wherein said time varying amplification means comprises a digital gain control means to generate a family of time varying gain curves.

14. The apparatus of claim 13 wherein said time varying amplification means is constructed and arranged to permit first detection of the far end of the pipe by emphasizing far signal returns above near signal returns.

15. An electronic signal processing apparatus which generates a family of time varying curves for use in a device for determining the length of a pipe, comprising:

(a) a time varying gain amplification means for generating a time varying gain curve; and (b) a separate means for acoustically generating a family of time varying gain curves, including a digital gain amplification means operating separately from and in conjunction with said time varying gain amplification means to generate said family of time varying curves.

* * * * *

UNITED STATES PATENT AND TRADEMARK OFFICE
CERTIFICATE OF CORRECTION

PATENT NO. : 4,935,884
DATED : June 19, 1990
INVENTOR(S) : David J. Hajicek

It is certified that error appears in the above-identified patent and that said Letters Patent is hereby corrected as shown below:

Column 1, line 58, after "floor", insert --.--.

Column 4, line 51, delete "an".

Column 5, line 35, after "end", insert --,--.

Column 5, line 36, before "come", insert --far end will--.

Column 5, line 68, delete "0", and substitute therefor --θ--.

Signed and Sealed this

Twenty-third Day of July, 1991

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,935,884
DATED : June 19, 1990
INVENTOR(S) : David J. Hajicek

It is certified that error appears in the above-identified patent and that said Letters Patent is hereby corrected as shown below:

Column 1, line 58, after "floor", insert --.--.

Column 4, line 51, delete "an".

Column 5, line 35, after "end", insert --,--.

Column 5, line 36, before "come", insert --far end will--.

Column 5, line 68, delete "0", and substitute therefor --0--.

Signed and Sealed this

Twenty-third Day of July, 1991

Attest:

HARRY F. MANBECK, JR.

*Attesting Officer*  *Commissioner of Patents and Trademarks*